(12) United States Patent
Mitchell et al.

(10) Patent No.: US 6,603,055 B2
(45) Date of Patent: *Aug. 5, 2003

(54) POLY (VINYLAMINE) - BASE SUPERABSORBENT GELS AND METHOD OF MANUFACTURING THE SAME

(75) Inventors: Michael A. Mitchell, Lake Zurich, IL (US); Thomas W. Beihoffer, Arlington Heights, IL (US); Raffat S. Sultana, Algonquin, IL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 191 days.

This patent is subject to a terminal disclaimer.

(21) Appl. No.: 09/746,177

(22) Filed: Dec. 22, 2000

(65) Prior Publication Data

US 2001/0007064 A1 Jul. 5, 2001

Related U.S. Application Data

(63) Continuation-in-part of application No. 09/179,554, filed on Oct. 28, 1998, now Pat. No. 6,194,631, which is a continuation-in-part of application No. 08/974,119, filed on Nov. 19, 1997, now Pat. No. 5,981,689.

(51) Int. Cl.[7] .............................. A61F 13/15; C08L 8/00
(52) U.S. Cl. .................... 604/372; 603/368; 525/191; 525/206; 525/218; 525/221
(58) Field of Search .................... 504/364, 367, 504/368, 372, 375; 525/191, 206, 218, 221; 428/327, 402, 407

(56) References Cited

U.S. PATENT DOCUMENTS

| | | |
|---|---|---|
| 4,569,344 A | 2/1986 | Palmer |
| 4,638,539 A | 1/1987 | Palmer |
| 4,696,296 A | 9/1987 | Palmer |
| 4,850,350 A | 7/1989 | Jackson |
| 5,073,164 A | 12/1991 | Hollister et al. |
| 5,083,561 A | 1/1992 | Russo |
| 5,125,893 A | 6/1992 | Dryden |
| 5,139,018 A | 8/1992 | Brodsky et al. |
| 5,269,756 A | 12/1993 | Dryden |
| 5,279,549 A | 1/1994 | Ranford |
| 5,309,902 A | 5/1994 | Kee et al. |
| 5,333,606 A | 8/1994 | Schneider et al. |
| 5,349,950 A | 9/1994 | Ulrich et al. |
| 5,449,348 A | 9/1995 | Dryden |
| 5,641,184 A | 6/1997 | Mortensen |
| 6,072,101 A * | 6/2000 | Beihoffer et al. ........... 604/372 |
| 6,222,091 B1 * | 4/2001 | Beihoffer et al. ........... 604/368 |

* cited by examiner

Primary Examiner—Weilun Lo
Assistant Examiner—Michael G. Bogart
(74) Attorney, Agent, or Firm—Marshall, Gerstein & Borun

(57) ABSTRACT

Bi-component superabsorbent materials are disclosed. The superabsorbent materials comprise a mixture of about 20% to about 40%, by weight, poly(vinylamine) polymer or other basic resin and about 60% to about 80%, by weight of an acidic water-absorbing polymer, like polyacrylic acid.

33 Claims, 8 Drawing Sheets

POLY (VINYLAMINE) - BASE SUPERABSORBENT GELS AND METHOD OF MANUFACTURING THE SAME

CROSS-REFERENCE TO RELATED APPLICATIONS

This is a continuation-in-part application of U.S. application Ser. No. 09/179,554, filed Oct. 28, 1998, now U.S. Pat. No. 6,194,631, which is a continuation-in-part application of U.S. application Ser. No. 08/974,119, filed Nov. 19, 1997, now U.S. Pat. No. 5,981,689.

FIELD OF THE INVENTION

The present invention relates to superabsorbent gels containing a poly(vinylamine), or a salt thereof, and to an improved method of manufacturing a poly(vinylamine). The superabsorbent gels comprise a basic superabsorbent polymer, and preferably a poly(vinylamine), in an amount of about 20% to about 40% by weight of superabsorbent polymers, admixed with an acidic superabsorbent polymer, like a polyacrylic acid, or comprise a salt of a poly(vinylamine).

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. No. 5,669,894. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, like a diaper.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers do not function as effective SAPs in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, like urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, like urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

Prior investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, like polyacrylic acid, and an amount of an ionizable surfactant sufficient to form at least a monolayer of surfactant on the polymer. In another embodiment, a cationic gel, like a gel containing quaternized ammonium groups and in the hydroxide (i.e., OH) form, is used with an anionic gel (i.e., a polyacrylic acid) to remove electrolytes from the solution by ion exchange.

Wong U.S. Pat. No. 4,818,598 discloses admixing a fibrous anion exchange material, like DEAE cellulose, and a hydrogel, like a polyacrylate, to improve absorption properties. WO 96/17681 discloses admixing an anionic SAP, like polyacrylic acid, with a polysaccharide-based cationic SAP to overcome the salt poisoning effect. Similarly, WO 96/15163 discloses admixing a cationic SAP having at least 20% of the functional groups in a basic (i.e., OH) form with a cationic exchanges resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect. It would be desirable, however, to provide an SAP that exhibits exceptional absorbency and retention, like a sodium polyacrylate, and, therefore, can be used alone as an SAP. It also would be desirable to admix such an SAP with polyacrylic acid, or another acid-containing SAP, to overcome the salt poisoning effect.

SUMMARY OF THE INVENTION

The present invention is directed to poly(vinylamine)-based superabsorbent gels. A poly(vinylamine) polymer can be used in conjunction with an acidic water-absorbing resin, like polyacrylic acid, to help overcome the salt poisoning effect, or a salt of a poly(vinylamine) polymer can be used alone as an SAP. The poly(vinylamine) polymer also can be used, alone, as an SAP to absorb and retain acidic media. More particularly, the poly(vinylamine) used as an SAP, or as a component of an SAP, is lightly crosslinked and, in preferred embodiments, is surface treated to improve absorption properties.

Accordingly, one aspect of the present invention is to provide an improved method of manufacturing a poly (vinylamine) comprising vinylamine monomer units, and which can be crosslinked using a suitable polyfunctional vinyl monomer. The present method substantially reduces the amount of residual N-vinylamide monomer in the poly (N-vinylamide) precursor of the poly(vinylamine), and, therefore, eliminates the stringent purification procedures, or reduces the long polymerization reaction times, previously used to overcome the problem of residual monomer content. Consequently, the present improved process reduces process time and production costs.

Another aspect of the present invention is to provide an SAP having absorbency and retention properties comparable to a conventional SAP, like sodium polyacrylate. A present SAP is produced by neutralizing a poly(vinylamine) with a sufficient amount of acid, like hydrochloric acid, such that at least about 10%, i.e., about 10% to 100%, of the amine-functional groups are neutralized. The resulting poly (vinylamine) salt is an excellent SAP for absorbing aqueous media.

In accordance with another important aspect of the present invention, a lightly crosslinked poly(vinylamine), alone and unneutralized, can be used to absorb and retain acidic aqueous media. The acidic aqueous media converts the low-absorbing poly(vinylamine) to a highly absorbing poly(vinylamine) salt, i.e., converts the polymer to an SAP, during absorption. A poly(vinylamine), therefore, is an excellent resin for cleaning acid spills and the remediation of acidic species.

Yet another aspect of the present invention is to provide an improved SAP that overcomes the salt poisoning effect of electrolytes. In particular, the improved SAP material contains a mixture of an acidic swellable resin, like polyacrylic acid, and about 20% to about 40%, by weight, of a poly (vinylamine), based on the total weight of the acidic resin and the poly(vinylamine).

Another aspect of the present invention is to provide an improved SAP material having improved absorption and retention properties compared to a conventional SAP, such as sodium polyacrylate. The present SAP material contains a low weight percentage of basic resin, e.g., about 20% to about 40% based on the total weight of acidic and basic resins, yet performs as well as an SAP material containing a significantly higher weight percent of basic resin. A present SAP material, therefore, provides economies by utilizing less of an expensive basic resin, while exhibiting excellent absorption and retention properties.

Yet another important feature of the present invention is to provide an SAP material containing about 60% to about 80%, by weight, of a weak acidic water-absorbing resin and about 20% to about 40%, by weight, of a weak basic water-absorbing resin, based on the total weight of the acidic and basic resin.

An example of a weak acidic resin is polyacrylic acid having 0% to 25% neutralized carboxylic acid groups (i.e., DN=0 to DN=25). Examples of weak basic water-absorbing resins are a poly(vinylamine), a poly(allylamine), and a polyethylenimine.

Still another aspect of the present invention is to provide articles of manufacture, like diapers and catamenial devices, having a core comprising an SAP material of the present invention. Other articles that can contain an SAP material of the present invention include adult incontinence products, and devices for absorbing saline and other ion-containing fluids.

These and other aspects and advantages of the present invention will become apparent from the following detailed description of the preferred embodiments.

DETAILED DESCRIPTION OF THE PREFERRED EMBODIMENTS

Figure 1:
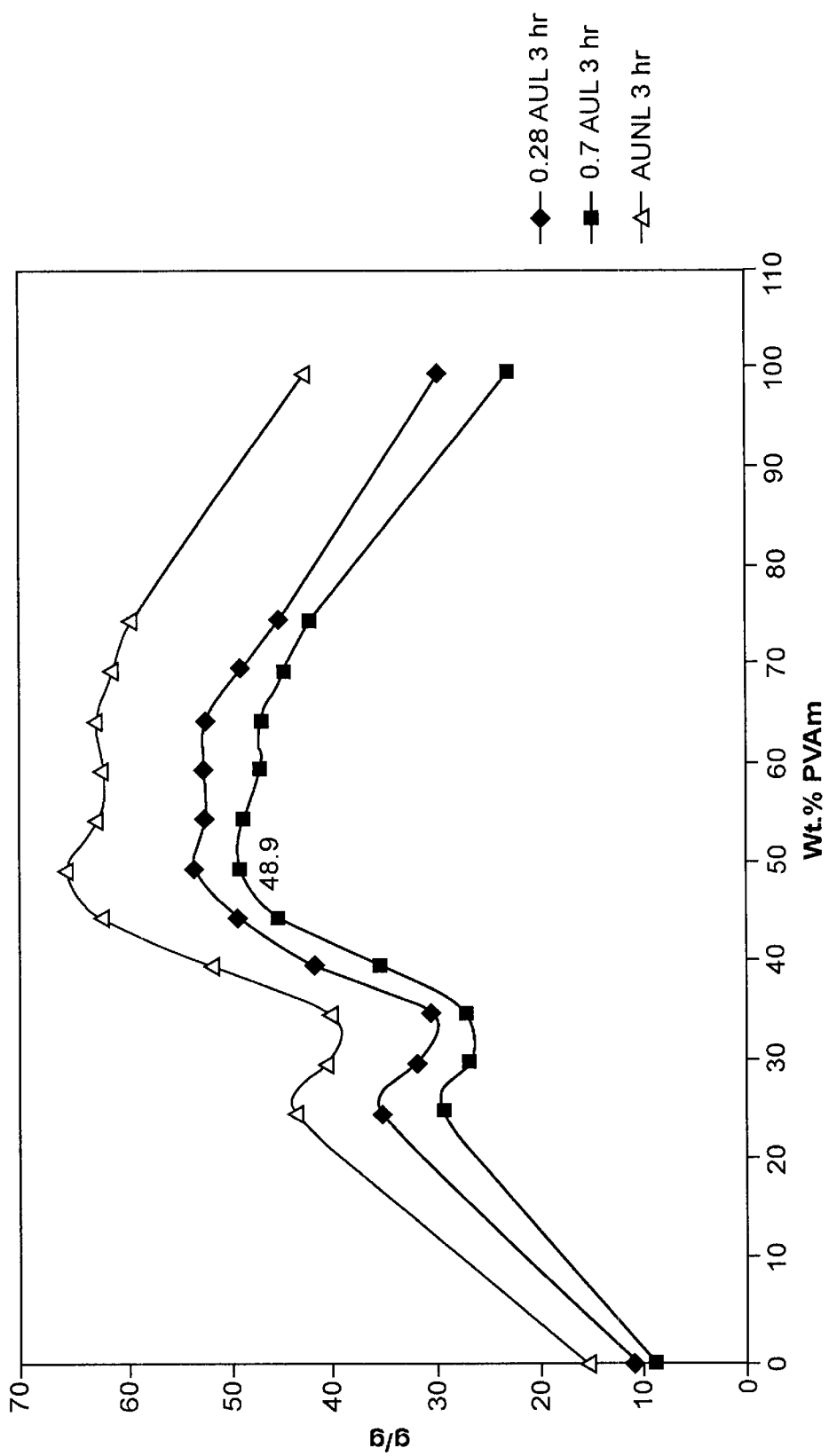
FIG. 1 contains plots of wt % poly(vinylamine) in a superabsorbent material vs. AUL (0.28 psi) and (0.7 psi), and vs. AUNL, in g/g, after 3 hours.

The present invention is directed to: (a) an improved method of manufacturing poly(vinylamine), (b) poly (vinylamine) and poly(vinylamine) salts and their use as SAPs, and (c) an improved SAP material comprising an admixture of an acidic water-absorbing resin and about 20% to about 40%, by weight, based on the total weight of the basic and acidic resin, of a poly(vinylamine) or other basic water-absorbing resin.

(a) An Improved Method of Manufacturing Poly (Vinylamine)

Poly(vinylamine), and salts derived therefrom, are known polymers. For example, the following patents disclose the synthesis or manufacture of poly(vinylamine): U.S. Pat. No. 4,798,871; U.S. Pat. No. 4,843,118; and U.S. Pat. No. 4,804,793. In addition, U.S. Pat. No. 4,018,826 discloses a process for preparing poly(vinylamine) and salts thereof. Ford et al. U.S. Pat. No. 5,491,199 discloses the preparation of formate-free poly(vinylamine) by heating the polymer in the presence of transition metal catalyst.

The above patents generally disclose polymers of N-vinylformamide that subsequently are hydrolyzed. Upon hydrolysis, the poly(N-vinylformamide) is converted into a poly(vinylamine). Hydrolysis can be performed under acid or basic conditions. The cationic charge on the resulting vinylamine, i.e., the charge density, is related to the pH of the medium. At a low pH, the poly(vinylamine) is protonated and has a high cationic charge density. Conversely, at a high pH, the poly(vinylamine) is not protonated, and the polymer has a substantially reduced cationic charge density, if any.

In general, an uncrosslinked poly(vinylamine) is a water-soluble polymer that has many practical applications, such as in water treatment, personal care products, and ion exchange resins. Poly(vinylamine) is rendered water insoluble by a crosslinking the polymer. Although polyvinylamines, and salts thereof, are well known, it has not heretofore been suggested that such polymers can be used as an SAP.

Typically, a poly(vinylamine) polymer is produced by hydrolysis of poly(N-vinylformamide), under either acid or basic conditions. Poly(vinylamine) also can be produced from other poly(N-vinylamides), like poly(N-vinylacetamide), poly(N-vinylpropionamide), and poly(N-vinylsuccinamide). It is desirable that hydrolysis of the poly(vinylamide) is substantially to essentially complete, i.e., about 10% to 100% complete, and preferably about 30% to 100% complete. To achieve the full advantage of the present invention, at least about 50%, and more preferably at least about 90%, of the amide groups are hydrolyzed to an amine functionality. The amine-functional polymer can contain other copolymerizable units, i.e., other monoethylenically unsaturated monomers, as long as the polymer is substantially, i.e., at least 10%, and preferably at least 25%, vinylamine units. To achieve the full advantage of the present invention, the polymer contains at least 50%, and more preferably at least 75%, vinylamine units.

If residual monomer or other impurities are present in the poly(vinylamide), hydrolysis conditions can lead to a crosslinking, which increases the molecular weight of the poly(vinylamine) and can result in undesirable and unpredictable gel formation. Therefore, current methods of synthesizing poly(vinylamine) require either a rigorous purification of the poly(N-vinylformamide), or an extremely long reaction time and a relatively high reaction temperature to ensure that all the residual poly(N-vinylformamide) monomer is consumed during the polymerization.

The production of poly(vinylamine) would be facilitated, and production costs decreased, by an improved method of removing residual N-vinylamide monomers from the poly (N-vinylamide). Therefore, in accordance with an important feature of the present invention, an improved method of manufacturing poly(vinylamine) is disclosed.

As set forth above, polymerization of N-vinylformamide, followed by hydrolysis, is the most common method of producing poly(vinylamine). The polymerization can be performed in the presence or absence of a crosslinker, i.e., a polyfunctional organic compound. However, residual N-vinylformamide monomer, or other monomer impurities, like aldehydes, can cause crosslinking and undesired gel formation during hydrolysis. In accordance with an important feature of the present invention, it has been found that the problem of residual monomer content, and the presence of other impurities, can be overcome by the use of suitable scavenging agents to remove the residual monomer and other impurities from the poly(N-vinylamide). The use of scavenging agents has the advantage of greatly reducing the process time, and costs, currently invested to insure that all the N-vinylamide monomer and other impurities are consumed prior to hydrolysis.

In accordance with an important feature of the present invention, a scavenging agent is added to a poly(N-vinylamide), prior to hydrolysis, in an amount of about 0.1% to about 3%, and preferably about 0.1% to about 2%, by weight, based on the weight of N-vinylamide monomer used in the polymerization. To achieve the full advantage of the present invention, the scavenging agent is added in an amount of about 0.1% to about 1%, by weight, based on the weight of N-vinylamide monomer.

The scavenging agent can be any compound capable of reacting with N-vinylamides, like N-vinylformamide, and other aldehydic impurities, like formaldehyde or acetaldehyde, under hydrolysis conditions, i.e., a temperature of about 25° C. to about 80° C. for about 4 to about 24 hours in the presence of an acid or a base. Typically, a scavenging agent is capable of reacting with an aldehyde in about 1 minute to about 10 minutes at a temperature of about 20° C. to about 80° C.

Examples of scavenging agents include, but are not limited to: (a) oxidizing agents, like potassium permanganate, ammonia silver salts (Tollen's Reagent), potassium dichromate, and hydrogen peroxide; (b) reducing agents, like catalytic hydrogenation, lithium aluminum hydride, sodium borohydride, diborane, aluminum hydride, $LiAlH(O\text{ }t\text{-}Bu)_3$ (lithium aluminum tri-t-butoxy hydride), $LiAlH(OCH_3)_3$ (lithium aluminum trimethoxy hydride), zinc (mercury) and concentrated hydrochloric acid, and hydrazine and a base; (c) Grignard reagents, like aryl and alkyl magnesium halides; (d) sodium or potassium cyanide with sodium bisulfite; (e) sodium bisulfite; and (f) ammonia derivatives, like hydroxylamine, hydrazine, substituted hydrazines, e.g., phenyl hydrazine, and semicarbazine. A reducing agent is a preferred scavenging agent, and sodium borohydride is a most preferred scavenging agent. Such scavenging agents have the advantages of being inexpensive, greatly reducing the reaction time to form a poly(N-vinylamide), and eliminating the need to purify the poly(N-vinylamide).

To achieve the full advantage of the present invention, the scavenging agent is an aqueous solution containing sodium borohydride, e.g., about 10% to about 15% by weight, and sodium hydroxide. The sodium borohydride acts quickly, is highly effective, and is inexpensive. As an added advantage, the sodium hydroxide is useful in a subsequent basic hydrolysis of the poly(N-vinylamide). Prior to hydrolyzing the poly(N-vinylamide), the poly(N-vinylamide) and scavenging agent are held at about 25° C. to about 80° C. for about 1 minute to about 10 minutes to eliminate essentially all, i.e., about 95% to 100%, of the residual monomers and impurities.

After using a scavenging agent to remove residual monomers and other impurities, the poly(N-vinylamide) is hydrolyzed. The amount of acid or base used to hydrolyze the poly(N-vinylamide) in solution can vary widely, and is generally added in a molar ratio of acid or base to N-vinylamide monomer content of the initially formed polymer of about 0.05:1 to about 3:1, preferably of about 0.3:1 to about 1:1. To achieve the full advantage of the present invention, the molar ratio of acid or base to N-vinylamide monomer is about 0.7:1 to about 1:1.

Generally, hydrolysis is achieved with a suitable acid, such as an inorganic acid, for example, hydrochloric acid, hydrobromic acid, hydrofluoric acid, sulfuric acid, nitric acid, phosphoric acid, and the like. In addition, suitable bases, such as an inorganic base, for example, sodium hydroxide, ammonia, ammonium hydroxide, potassium hydroxide, and the like, can also be used. Hydrolysis is conducted at a temperature of about 25° C. to about 100° C. for about 4 to about 24 hours.

The degree of hydrolysis is controlled by the amount of acid or base, the reaction temperature, and/or the reaction time. In general, greater amounts of acid or base, higher reaction temperatures, and longer reaction times result in higher degrees of hydrolysis.

The present method, therefore, is an improved method of manufacturing either crosslinked or uncrosslinked poly (vinylamine). The following examples illustrate the improved method in the manufacture of uncrosslinked poly (vinylamine).

EXAMPLE 1

N-vinylformamide (400 g, 5.6 mole) was dissolved in 3,000 g of deionized water, then the resulting monomer solution was sparged with argon for one hour. In a separate vessel, 5 g of 2,2'-azobis(2-amidinopropane)hydrochloride initiator (i.e., V-50 initiator available from Wako Pure Chemical Industries, Inc., Osaka, Japan) was dissolved in 70 g of deionized water, then the resulting initiator solution was sparged with argon for one-half hour. A 7 g portion of the initiator solution was added to the monomer solution, and the remainder of the initiator solution was added to the monomer solution over an hour period while heating the resulting reaction mixture to about 45° C. The reaction temperature was maintained at about 45° C. for about 4 hours. The reaction mixture then was heated to 55° C. and held for two hours. Finally, 20 g of a 15% by weight aqueous V-50 solution was added to the reaction mixture, and the polymerization reaction was held at 65° C. for 12 hours to provide poly(N-vinylformamide).

The aqueous poly(N-vinylformamide) solution then was heated to about 70° C., while 20 g of a 12% by weight sodium borohydride solution (in 41% aqueous sodium hydroxide) was added to the polymer solution. After the scavenger solution was added, 480 g of 50% aqueous sodium hydroxide was added to the polymer solution, and the resulting solution was stirred for about 8 hours at about 70° C. to hydrolyze the poly(N-vinylformamide).

If desired, the resulting poly(vinylamine) solution then can be purified by ultrafiltration. In this optional purification, the poly(vinylamine) solution was diluted with 3 liters of deionized water. The diluted solution then was ultrafiltered with a 100,000 molecular weight cut-off tangential flow ultrafiltration module. The diluted polymer solution was washed with 25 liters of deionized water, and then concentrated to 2,500 ml to give a 4 wt % solution of sodium formate-free poly(vinylamine).

Example 1 was repeated, but the scavenger step using sodium borohydride was omitted. During hydrolysis, the aqueous solution of poly(N-vinylformamide) gelled. Gelling was attributed to impurities present in the N-vinylformamide monomer that were not removed in a scavenging step.

The following example illustrates the ability of a scavenger, like sodium borohydride, to reduce the reaction time in the synthesis of a poly(vinylamine).

EXAMPLE 2

A five liter flask was charged with 400 g of N-vinylformamide monomer and 2,970 g of deionized water, and the resulting monomer solution was sparged with argon for one hour. Separately, an initiator solution was prepared by dissolving 5 g of V-50 in 67 g of deionized water, and sparging with argon for 0.5 hours. A portion of the initiator solution (7 g) was added to the monomer solution. The remainder of the initiator solution was added to the monomer solution over a one-hour time period, while the resulting reaction mixture was heated to 45° C. The reaction mixture was held at 45° C. for 2.5 hours, then heated to 55° C. and held for an additional 2.5 hours, and finally heated to 65° C. and held for an additional one hour. Next, 20 g of 12% sodium borohydride in a 41% aqueous sodium hydroxide solution was added to the reaction mixture, followed immediately by 480 g of a 50% aqueous sodium hydroxide solution. The reaction mixture quickly turned pink in color but then returned to colorless. The hydrolysis step was continued at 70° C. for an additional 8 hours. The resulting poly(vinylamine) solution can then be purified, if desired, by ultrafiltration as set forth in Example 1. In the absence of a sodium borohydride scavenger, the reaction requires an additional several hours to react all the N-vinylformamide monomers and other impurities, as set forth in Example 1.

EXAMPLE 3

Freshly distilled N-vinylformamide (250 g, 3.5 mole) and 2.8 g of 15% V-50 initiator were dissolved in 400 g of deionized water, then the resulting reaction solution was sparged with argon for 15 minutes. Next, the reaction solution was poured into a glass pan and cured at 15 mW/cm$^2$ of UV light for 25 minutes. The polymerization was exothermic, eventually reaching about 100° C. The resulting concentrated poly(N-vinylformamide) solution was very viscous.

The concentrated poly(N-vinylformamide) solution (312 g) then was diluted with 2 liters of deionized water, and the diluted polymer solution was heated to 70° C. Six (6) g of a sodium borohydride solution (15% by weight of 41% aqueous sodium hydroxide) was added dropwise to the heated polymer solution over a five-minute time period, followed by the addition of 143 g of 50% aqueous sodium hydroxide. The resulting solution was maintained at 70° C. for 8 hours to hydrolyze the poly(N-vinylformamide), then cooled and purified as in Example 1.

The present improved method of manufacturing poly (vinylamine) also can be used in processes wherein poly (vinylamine) is derived from, for example, poly(N-vinylacetamide), poly(N-vinylpropionamide), poly(N-vinylsuccinamide), and similar N-vinylcarboxamides.

The present improved method of manufacturing a poly (vinylamine) can also be used in the manufacture of a crosslinked poly(vinylamine). As described above, SAPs are crosslinked to a sufficient extent such that the polymer is water insoluble. Crosslinking serves to render the poly (vinylamine) polymers substantially water insoluble, and, in part, serves to determine the absorptive capacity of the polymers. For use in absorption applications, the poly (vinylamine) is lightly crosslinked, i.e., has a crosslinking density of less than about 20%, and preferably less than about 10%, and most preferably about 0.01% to about 7%.

When used, a crosslinking agent most preferably is included in an amount of less than about 7 wt %, and typically about 0.1 wt % to about 5 wt %, based on the total weight of monomers. A poly(vinylamine) can be crosslinked by two different pathways. One pathway utilizes olefinically unsaturated crosslinking monomers that copolymerize with the N-vinylamide, and, therefore, form a part of the polymeric backbone. The crosslinked poly(N-vinylamide) then is hydrolyzed to provide crosslinked polyvinylamine.

Examples of crosslinking polyvinyl monomers include, but are not limited to, polyacrylic (or polymethacrylic) acid esters represented by the following formula (I); and bisacrylamides, represented by the following formula (II).

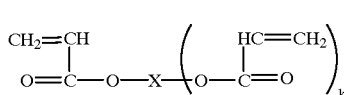

(I)

wherein x is ethylene, propylene, trimethylene, hexamethylene, 2-hydroxypropylene, —$(CH_2CH_2O)_n$—$CH_2CH_2$', or

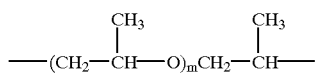

n and m are each an integer 5 to 40, and k is 1 or 2;

(II)

wherein 1 is 2 or 3.

The compounds of formula (I) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (II) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides or mixtures thereof. Compounds like divinylbenzene and divinyl ether also can be used to crosslink the poly(N-vinylamide). Especially preferred crosslinking agents are N,N'-methylenebisacrylamide, N,N'-methylenebismethacrylamide, ethylene glycol dimethacrylate, and trimethylolpropane triacrylate.

The following example illustrates a cross-linked poly(vinylamine) prepared in accordance with the present invention.

EXAMPLE 4

A monomer mixture containing N-vinylformamide (250 grams), deionized water (250 grams), methylenebisacrylamide (1.09 grams), and V-50 initiator (0.42 grams) was placed in a shallow dish, then polymerized under an ultraviolet lamp as set forth in Example 3 until the mixture polymerized into a rubbery gel. The concentrated poly(N-vinylformamide) then was treated with a sodium borohydride/sodium hydroxide solution, as set forth in Example 1, to yield a lightly crosslinked poly(vinylamine). Sodium formate present in the crosslinked poly(vinylamine) can be removed by washing the resin with acetone/water mixtures, or by other suitable methods known to persons skilled in the art.

Poly(vinylamine) also can be crosslinked in solution by suspending or dissolving uncrosslinked poly(vinylamine) in an aqueous medium, then adding a di- or poly-functional compound capable of crosslinking the poly(vinylamine) by reaction with the amino groups of the polymer. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $WS(O_2)O$—$(CH_2)_n$—$OF(O)_2W$, wherein n is one to 10, and W is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate). Crosslinking agents also are disclosed in Pinschmidt, Jr. et al. U.S. Pat. No. 5,085,787, incorporated herein by reference, and in EP 450 923.

In general, the crosslinking agent should be water soluble and possess sufficient reactivity with poly(vinylamine) such that crosslinking occurs in a controlled fashion, preferably at a temperature of about 25° C. to about 150° C. A preferred crosslinking agent is ethylene glycol diglycidyl ether (EGDGE), a water-soluble diglycidyl ether.

The following example illustrates light crosslinking of a sodium formate-free poly(vinylamine) of the present invention using a polyfunctional crosslinking agent that reacts with the amino groups of the polymer.

EXAMPLE 5

To 2 liters of a 3% by weight aqueous poly(vinylamine) solution was added 0.18 g of ethyleneglycol diglycidyl ether (EGDGE). The resulting mixture was stirred to dissolve the EGDGE, then the mixture was heated to about 60° C. and held for one hour to gel. The gel was heated to about 80° C. and held until about 90% of the water was removed. The resulting gel then was extruded and dried to a constant weight at 80° C. The dried, lightly crosslinked poly(vinylamine) then was cryogenically milled to form a granular material capable of absorbing water or acid solutions. The gel exhibited the following absorption characteristics in 0.1 M hydrochloric acid (HCl):

$AUNL^{1)}$=59.3 g/g $AUL^{2)}$ (0.28 psi)=37.8 g/g $AUL^{2:}$ (0.7 psi)=26.4 g/g

[1] Absorption under no load; and
[2] Absorption under load.

Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g±0.001 g) is carefully scattered onto a 140-micron, water-permeable mesh attached to the base of a hollow plexiglass cylinder with an internal diameter of 25 mm. The sample is covered with a 100 g cover plate and the cylinder assembly weighed. This gives an applied pressure of 20 g/cm$^2$ (0.28 psi). Alternatively, the sample can be covered with a 250 g cover plate to give an applied pressure of 51 g/cm$^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact. As discussed hereafter, the poly(vinylamine) particles also can be surface treated with a crosslinking agent, like ethyleneglycol diglycidyl ether, to give an absorbent having improved performance under external pressure.

In a preferred embodiment, a lightly crosslinked poly(vinylamine) is subjected to a process step wherein the surface of the poly(N-vinylamine) is further crosslinked. It has been found that surface crosslinking of a poly(vinylamine) enhances the ability of the polymer to absorb and retain aqueous media under load.

Surface crosslinking is achieved by spraying poly(vinylamine) particles with an isopropyl alcohol solution of a surface crosslinking agent to wet predominantly only the outer surfaces of the poly(vinylamine) particles. Surface crosslinking and drying of the polymer then is performed, preferably by heating at least the wetted surfaces of the poly(vinylamine) particles.

Typically, the poly(vinylamine) particles are surface treated with an alcoholic solution of a surface crosslinking agent. The particles can be in the form of granules, a foam, beads, flakes, fibers, or powders, for example. The solution contains about 0.01% to about 4%, by weight, surface crosslinking agent, and preferably about 0.4% to about 2%, by weight, surface crosslinking agent in a suitable solvent. The solution can be applied as a fine spray onto the surface of freely tumbling poly(vinylamine) particles at a ratio of about 1:0.01 to about 1:0.5 parts by weight poly(vinylamine) to solution of surface crosslinking agent. The surface crosslinker is present in an amount of 0% to about 1%, by weight of the poly(vinylamine), and preferably 0% to about 0.5% by weight. To achieve the full advantage of the present invention, the surface crosslinker is present in an amount of about 0.001% to about 0.1% by weight.

The crosslinking reaction and drying of the surface-treated poly(vinylamine) particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the poly(vinylamine) particle, and any other method of drying the poly(vinylamine) particles, such as microwave energy, or the like, can be used.

Suitable surface crosslinking agents include the di- or poly-functional molecules capable of reacting with amino groups and crosslinking poly(vinylamine). Preferably, the surface crosslinking agent is alcohol or water soluble and possesses sufficient reactivity with a poly(vinylamine) such that crosslinking occurs in a controlled fashion at a temperature of about 25° C. to about 150° C.

Nonlimiting examples of suitable surface crosslinking agents include:

(a) dihalides and disulfonate esters, for example, compounds of the formula

wherein p is a number from 2 to 12, and Z, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, like epichlorohydrin;

(e) multifunctional epoxy compounds, for example, ethylene glycol diglycidyl ether, bisphenol A diglycidyl ether, and bisphenol F diglycidyl ether;

(f) multifunctional carboxylic acids and esters, acid chlorides, and anhydrides derived therefrom, for example, di- and poly-carboxylic acids containing two to twelve carbon atoms, and the methyl and ethyl esters, acid chlorides, and anhydrides derived therefrom, like oxalic acid, adipic acid, succinic acid, dodecanoic acid, malonic acid, and glutaric acid, and esters, anhydrides, and acid chlorides derived therefrom;

(g) organic titanates, like TYZOR AA, available from E. I. DuPont de Nemours, Wilmington, Del.;

(h) melamine resins, like the CYMEL resins available from Cytec Industries, Wayne, N.J.;

(i) hydroxymethyl ureas, like N,N'-dihydroxymethyl-4,5-dihydroxyethylene urea; and (j) multifunctional isocyanates, like toluene diisocyanate, isophorone diisocyanate, xylene diisocyanate, and hexamethylene diisocyanate.

A preferred surface crosslinking agent is ethylene glycol diglycidyl ether (EGDGE), which is a water-soluble diglycidyl ether which crosslinks poly(vinylamine) at a temperature of about 25° C. to about 150° C.

The following Example 6 illustrates surface treatment and crosslinking of a lightly crosslinked poly(vinylamine).

EXAMPLE 6

Divinylbenzene crosslinker (1.085 g, 55% active, by weight, in styrene/ethylstyrene), aqueous V-50 initiator (2.541 g, 15%), and N-vinylformamide (245 g, 3.45 moles) were mixed in 350 g of deionized water. The resulting solution was sparged with argon for 15 minutes, and then polymerized under UV light (15 mW/cm$^2$) for one hour. The resulting gel was extruded, dried at 100° C., and milled to produce particles of lightly crosslinked poly(vinylamine).

A portion of the poly(N-vinylformamide) particles (82 g) was hydrolyzed by dispersing the particles in a solution containing 168 g cyclohexane, 112 g 1-butanol, and 46 g of powdered sodium hydroxide. The resulting suspension then was heated at about 70° C. for about 6 hours. Next, 150 g of deionized water was added to the suspension, and the organic solvents were decanted. Acetone (230 g) then was added to collapse the gel and remove the sodium formate by-product. The water/acetone wash was repeated three more times, and the gel was dried then remilled. The resulting poly(vinylamine) gel then was surface treated with ethylene glycol diglycidyl ether at various levels, and dried at 145° C. to provide a surface crosslink.

The poly(vinylamine) then was tested for an ability to absorb and retain 0.1 M hydrochloric acid.

TABLE 1

| Surface crosslink Level (ppm)[3] | AUNL[1] and AUL[2] (0.1M HCl) | | |
|---|---|---|---|
| | No Load | 0.28 psi | 0.7 psi |
| 0 | 51 | 23 | 9.9 |
| 100 | 47 | 27 | 19 |
| 500 | 47 | 27 | 19 |
| 1000 | 46 | 28 | 20 |
| 2000 | 41 | 26 | 20 |

[3]ppm--parts per million of surface crosslinker.

The absorption data shows that surface crosslinking substantially improves the absorption under load of a poly (vinylamine), especially at a load of 0.7 psi.

(b) Poly(Vinylamine)-Based SAPs

Poly(vinylamine) typically does not function as an SAP in its neutral form because there is no ionic charge on the polymer. The driving force for water absorption and retention therefore is lacking. However, when converted to a salt, or used in conjunction with an acidic water-absorbing resin, like a polyacrylic acid, a poly(vinylamine) then behaves likes an SAP. It should be understood that a poly (vinylamine) produced either by the above-described improved method, or by a prior, conventional method, can be used in a poly(vinylamine)-based SAP.

(i) Salts of Poly(Vinylamine)

As previously discussed, sodium poly(acrylate) is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

Poly(vinylamine) is a neutral polymer, and, accordingly, does not possess the polyelectrolytic properties necessary to provide an SAP. However, poly(vinylamine) salts have polyelectrolytic properties sufficient to provide an SAP. The poly(vinylamine) used to provide an SAP is a lightly crosslinked poly(vinylamine), and preferably is surface crosslinked, as set forth above.

Such lightly crosslinked, and optionally surface crosslinked, poly(vinylamine) polymers are converted into salts by methods known in the art. For example, the preparation of poly(vinylamine HCl) by the addition of hydrochloric acid to a poly(vinylamine) is set forth in Pinschmidt, Jr. et al. U.S. Pat. No. 5,085,787, and in Gless, Jr. et al. U.S. Pat. No. 4,018,826, or by hydrolysis of a poly(N-vinylamide) with hydrochloric acid.

A poly(vinylamine) salt useful as an SAP, however, is not limited to the hydrochloride salt. Poly(vinylamine) can be reacted with a variety of acids to provide a poly(vinylamine) salt useful as an SAP, but the preferred acids are mineral acids. To achieve the full advantage of the present invention, the poly(vinylamine) salt is a hydrochloride salt.

To demonstrate the ability of a poly(vinylamine) salt to act as an SAP, the lightly crosslinked poly(vinylamine) of Example 5 was converted to the hydrochloride salt by methods well known in the art. The poly(vinylamine) salt was tested for its ability to absorb and retain deionized water and electrolyte-containing aqueous media (i.e., 0.9% by weight aqueous sodium chloride).

In particular, poly(vinylamine) samples, as prepared in Example 5, were converted to the hydrochloride salt using different amounts of 1N hydrochloric acid (HCl). The resulting gels of poly(vinylamine) salt then were dried and evaluated for an ability to absorb a 0.9% by weight aqueous NaCl solution. The results are summarized in Table 2.

TABLE 2

| Mole % HCL[4] | AUNL[1] | AUL[2] (0.28 psi) | AUL[2] (0.7 psi) |
|---|---|---|---|
| 0 | 18.7 | 13.7 | 12.6 |
| 30 | 31.6 | 21.5 | 15.9 |
| 50 | 39.8 | 25.6 | 20.1 |
| 70 | 43.0 | 23.4 | 13.5 |
| 100 | 28.5 | 9.1 | 9.5 |

[4]mole % HCl added to the poly(vinylamine) based on the moles of N-vinylformamide monomer used to prepare the poly(vinylamine).

The absorbency results summarized in Table 2 show that absorbency increases dramatically, both under load and under no load, when the poly(vinylamine) is converted to a hydrochloride salt, especially in the range of about 30 to about 70 mole % conversion to the salt. In accordance with an important feature of the present invention, a polyl (vinylamine) exhibits the properties of an SAP when converted to a salt in an amount of about 10 to about 100, and preferably about 20 to about 90, mole percent. To achieve the full advantage of the present invention, the poly (vinylamine) is converted to a salt in an amount of about 25 to about 75 mole %, based on the weight of N-vinylamide monomer used to prepare the poly(vinylamine).

In another test, a lightly crosslinked poly(vinylamine), as prepared in Example 6, was surface treated with various levels of ethylene glycol diglycidyl ether (EGDGE) in isopropyl alcohol, followed by drying and curing at 80° C. The surface crosslinked granules of lightly crosslinked polyvinylamine then were partially neutralized (i.e., 50 mole %) with 1N HCl. The surface crosslinked polyvinylamine salt, then was tested for an ability to absorb and retain a 0.9% aqueous NaCl solution. The results are summarized in Table 3, and show that a neutralized and surface crosslinked poly(vinylamine) shows an improvement in AUL.

TABLE 3

| Surface crosslink Level of EGDGE (ppm)[4] | AUNL[1] | AUL[2] (0.28 psi) | AUL[2] (0.7 psi) |
|---|---|---|---|
| 0 | 35.8 | 16.6 | 9.3 |
| 100 | 35.3 | 18.9 | 11.3 |
| 500 | 31.5 | 16.3 | 11.2 |
| 1000 | 31.3 | 17.8 | 11.5 |
| 2000 | 28.8 | 18.0 | 11.9 |

(ii) Poly(Vinylamine) in SAPs

As illustrated above, poly(vinylamine), in its free base form, does not function as an SAP for neutral-to-basic aqueous media. Similarly, polyacrylic acid, in its free acid form, does not function as an SAP for neutral-to-acidic aqueous media. In each case, the polymer has a low charge density, and, accordingly, a major driving force for absorption and retention, i.e., electrostatic repulsion, is missing. In contrast, partially neutralized polyacrylic acid has a sufficient charge density, and is currently used as an SAP by itself. Similarly, as disclosed above, poly(vinylamine) salts have a high charge density and are excellent SAPs.

However, a poly(vinylamine), in its free base form, can act as an absorbent for acidic aqueous media, i.e., media having a pH less than 7, as illustrated in Examples 5 and 6, wherein one gram of poly(vinylamine) absorbed 59.3 g and 51 g of 0.1 M hydrochloric acid under no load, respectively. The acidic media protonates the amino groups of the poly (vinylamine), thereby providing sufficient charge density for the protonated poly(vinylamine) to perform as an SAP. Accordingly, poly(vinylamine), by itself, can be used to absorb acidic aqueous media, for example, to absorb an acid spill.

It also has been found that poly(vinylamine) polymers, in their free base form, are useful components in superabsorbent materials further containing an acidic water-absorbing resin. For example, a superabsorbent material of the present invention is an admixture of a poly(vinylamine) and an acidic water-absorbing resin, like polyacrylic acid. The superabsorbent material contains a poly(vinylamine), or other basic water-absorbing resin, in an amount of about 20% to about 40%, by weight, based on the total weight of poly(vinylamine) and acidic water-absorbing resin. The present superabsorbent materials are particularly useful with respect to absorbing and retaining aqueous media containing electrolytes.

Currently, superabsorbent materials containing two absorbing components, i.e., bi-component SAP materials, are being investigated as an improved class of SAPs. Typically, one component is a water-absorbing resin, and the second component acts in an ion exchange capacity to remove electrolytes from an aqueous media.

In contrast, the present invention is directed to a bi-component SAP material comprising two uncharged, slightly crosslinked polymers, each of which is capable of swelling and absorbing aqueous media. When contacted with water, the two uncharged polymers neutralize each other to form a superabsorbent material. Neither polymer in its uncharged form behaves as an SAP by itself when contacted with water. The present bi-component superabsorbent material, therefore, contains two resins, one acidic and one basic, which are capable of acting as an absorbent material in their polyelectrolyte form. While polyacrylic acid is an excellent choice for the acidic resin, until the present invention, there has not been an adequate basic resin.

In accordance with an important feature of the present invention, a poly(vinylamine), or other basic water-absorbing resin, is present in the bi-component superabsorbent material in a low weight percent. The excellent absorption and retention properties exhibited by the present bi-component superabsorbent material is unexpected because the amount of poly(vinylamine), or other basic water-absorbing resin, is insufficient to neutralize the greater amount of acidic resin present in the bi-component superabsorbent material.

Therefore, in accordance with an important feature of the present invention, a poly(vinylamine) is used as the basic resin for a bi-component SAP material. Other basic resins useful in a bi-component SAP material in an amount of about 20% to about 40%, by weight of basic resin and acidic resin include, but are not limited to, poly(allylamine), poly (diallylamine), and poly(azetidine). The preferred basic resin is poly(vinylamine).

The poly(vinylamine) is lightly crosslinked, and the poly (vinylamine) particles preferably are surface crosslinked to improve absorbency characteristics. The poly(vinylamine), or other basic resin, and acidic resin mixture behaves like an SAP in the presence of water, and especially brackish water. The poly(vinylamine) can be prepared by the improved method disclosed herein, or by prior methods known in the art. Crosslinking and surface crosslinking can be performed as set forth above.

The poly(vinylamine) is a basic resin, particles of which are admixed with particles of an acidic resin, and as stated above, other basic resins also can be used. The acidic resin can be any resin that acts as an SAP in its neutralized form. The acidic resin typically contains a plurality of carboxylic acid, sulfonic acid, phosphonic acid, phosphoric acid, or sulfuric acid moieties, or a mixture thereof.

An acidic resin present in an SAP material of the present invention can be either a strong or a weak acidic water-absorbing resin. The acidic water-absorbing resin can be a single resin, or a mixture of resins. The acidic resin can be a homopolymer or a copolymer. The identity of the acidic resin is not limited as long as the resin is capable of swelling and absorbing at least ten times its weight in water, when in a neutralized form. The acidic resin is present in its acidic form, i.e., about 75% to 100% of the acidic moieties are present in the free acid form. As illustrated hereafter, although the free acid form of a acidic water-absorbing resin is generally a poor water absorbent, the combination of an acidic resin and a basic resin in a present SAP material provides excellent water absorption and retention properties.

The acidic water-absorbing resin typically is a lightly crosslinked acrylic-type resin, such as lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity of the polymer.

Ethylenically unsaturated carboxylic acid and carboxylic acid anhydride monomers useful in the acidic water-absorbing resin include, but are not limited to, acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, furmaric acid, tricarboxyethylene, and maleic anhydride.

Ethylenically unsaturated sulfonic acid monomers include, but are not limited to, aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, sulfopropyl methacrylate, 2-hydroxy-3-methacryloxypropyl sulfonic acid, and 2-acrylamide-2-methylpropane sulfonic acid.

As set forth above, polymerization of acidic monomers, and copolymerizable monomers, if present, most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters, represented by the following formula (III), and bisacrylamides, represented by the following formula (IV),

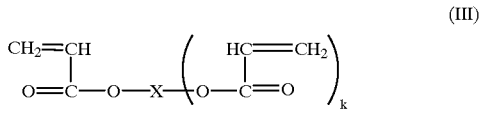
(III)

wherein x is ethylene, propylene, trimethylene, cyclohexyl, hexamethylene, 2-hydroxypropylene, —(CH$_2$CH$_2$O)$_n$CH$_2$CH$_2$—, or

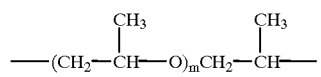

n and m are each an integer 5 to 40, and k is 1 or 2;

(IV)

wherein 1 is 2 or 3.

The compounds of formula (III) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (IV) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris (2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used as crosslinkers. Especially preferred crosslinking agents are N,N'-methylenebisacrylamide, N,N'-methylenebismethacrylamide, ethylene glycol dimethacrylate, and trimethylolpropane triacrylate.

The acidic resin, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The poly(vinylamine), or other basic resin, is present in its uncharged, i.e., free base, form, and the acidic resin is present in its free acid form. It is envisioned that a low percentage, i.e., 25% or less, of the basic and acidic functionalities can be in their charged form, due to processing, for example. The low percentage of charged functionalities does not adversely affect performance of the superabsorbent material, but the amount of charged functionalities should be minimized.

The poly(vinylamine), or other basic resin, and acidic resin are admixed in a weight ratio of about 20:60 to about 40:60, and preferably about 22:78 to about 35:65. To achieve the full advantage of the present invention, the resins are admixed in a weight ratio of about 25:75 to about 30:70. A present bi-component SAP material is prepared by simply admixing particles of the poly(vinylamine), or other basic resin, and particles of an acidic resin to provide a uniform particulate material.

Alternatively stated, a bi-component SAP material of the present invention contains a mole ratio of about 0.4:1 to about 0.9:1 of basic resin to acidic resin, and preferably a mole ratio of about 0.45:1 to about 0.85:1, based on the total amount of basic resin and acidic resin in the material. To achieve the full advantage of the present invention, the mole ratio of basic resin to acidic resin is about 0.55:1 to about 0.75:1.

Analogous to the acidic resin, the basic water-absorbing resin in the present bi-component SAP material is not limited to poly(vinylamine) and can be other strong or weak basic water-absorbing resins. The basic water-absorbing resin can be a single resin or a mixture of resins. The basic resin can be a homopolymer or a copolymer. The basic resin is capable of swelling and absorbing at least 10 times its weight in water, when in a charged form. The weak basic resin typically is present in its free base, or neutral, form, i.e., about 75% to about 100% of the basic moieties, e.g., amino groups, are present in a neutral, uncharged form. The strong basic resins typically are present in the hydroxide (OH) or bicarbonate (HCO$_3$) form.

The basic water-absorbing resin typically contains amino or guanidino moieties, such as a poly(vinylamine). The basic water-absorbing resin can be any polymer containing a primary amine, a secondary amine, or a hydroxy functionality. The basic resin, for example, can be a lightly crosslinked polyethylenimine, a poly(allylamine), a poly (diallylamine), a copolymer of a dialkylamino acrylate and a monomer having primary amino, secondary amino, or hydroxy functionality, a guanidine-modified polystyrene, such as

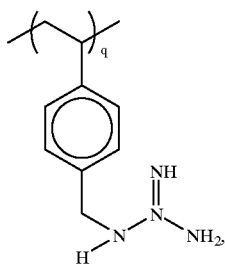

or a poly(vinylguanidine), i.e., poly(VG), a strong basic water-absorbing resin having the general structural formula (V)

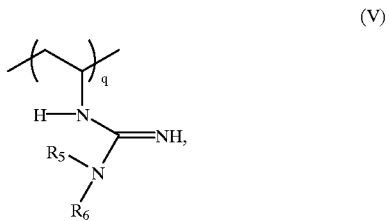

wherein q is a number from 10 to about 100,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups. The lightly crosslinked basic water-absorbing resin can contain other copolymerizable units and is crosslinked using a polyfunctional organic compound, as set forth above with respect to the acidic water-absorbing resin.

Examples of preferred basic resins include a poly(vinylamine), a polyethylenimine, a poly(vinylguanidine), a poly(allylamine), a poly(diallylamine), or a poly(allylguanidine). Preferred basic resins include poly(vinylamine), polyethylenimine, and poly(vinylguanadine). The most preferred basic resin is a poly(vinylamine), a poly(allylamine), or a poly(dialkylamine).

A basic water-absorbing resin used in the present bi-component SAP material typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZA(O_2)O-(CH_2)_n-OS(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate or methylene diisocyanate). Crosslinking agents also are disclosed in Pinschmidt, Jr. et al. U.S. Pat. No. 5,085,787, incorporated herein by reference, and in EP 450 923.

Conventionally, the crosslinking agent is water or alcohol soluble, and possesses sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

In preferred embodiments, the acidic resin, the basic resin, and/or the SAP material are surface treated. Surface treatment results in surface crosslinking of the particle. In especially preferred embodiments, the acidic and/or basic resins comprising the SAP material are surface treated and/or annealed, and the blended SAP material is surface treated. It has been found that surface treating of an acidic resin, a basic resin, and/or an SAP material of the present invention enhances the ability of the resins or SAP material to absorb and retain aqueous media under a load.

Surface crosslinking is achieved by contacting an acidic resin, a basic resin, and/or an SAP material with a solution of a surface crosslinking agent to wet predominantly only the outer surfaces of the resin particles. Surface crosslinking and drying of the resin particles then is performed, preferably by heating at least the wetted surfaces of the resin or multicomponent SAP particles.

Typically, the resins and/or SAP material are surface treated with a solution of a surface crosslinking agent. The solution contains about 0.01% to about 4%, by weight, surface crosslinking agent, and preferably about 0.4% to about 2%, by weight, surface crosslinking agent in a suitable solvent, for example, water or an alcohol. The solution can be applied as a fine spray onto the surface of freely tumbling resin particles of the SAP materials at a ratio of about 1:0.01 to about 1:0.5 parts by weight resin or SAP particles to solution of surface crosslinking agent. The surface crosslinker is present in an amount of 0% to about 5%, by weight of the resin or SAP material, and preferably 0% to about 0.5% by weight. To achieve the full advantage of the present invention, the surface crosslinker is present in an amount of about 0.001% to about 0.1% by weight.

The crosslinking reaction and drying of the surface-treated resin or SAP materials are achieved by heating the surface-treated polymer at a suitable temperature, e.g., about 25° C. to about 150° C., and preferably about 105° C. to about 120° C. However, any other method of reacting the crosslinking agent to achieve surface crosslinking of the resin or SAP material, and any other method of drying the resin or SAP material, such as microwave energy, or the such as, can be used.

With respect to the basic resin, suitable surface crosslinking agents include di- or polyfunctional molecules capable of reacting with amino or guanidino groups and crosslinking a basic resin. Preferably, the surface crosslinking agent is alcohol or water soluble and possesses sufficient reactivity with a basic resin such that crosslinking occurs in a controlled fashion at a temperature of about 25° C. to about 150° C.

Nonlimiting examples of suitable surface crosslinking agents for basic resins include:

(a) dihalides and disulfonate esters, for example, compounds of the formula

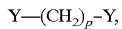

wherein p is a number from 2 to 12, and Y, independently, is halo (preferably bromo), tosylate, mesylate, or other alkyl or aryl sulfonate esters;

(b) multifunctional aziridines;
(c) multifunctional aldehydes, for example, glutaraldehyde, trioxane, paraformaldehyde, terephthaldehyde, malonaldehyde, and glyoxal, and acetals and bisulfites thereof;
(d) halohydrins, such as epichlorohydrin;
(e) multifunctional epoxy compounds, for example, ethylene glycol diglycidyl ether, bisphenol A diglycidyl ether, and bisphenol F diglycidyl ether,
(f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;
(g) organic titanates, such as TYZOR AA, available from E. I. DuPont de Nemours, Wilmington, Del.;
(h) melamine resins, such as the CYMEL resins available from Cytec Industries, Wayne, N.J.;
(i) hydroxymethyl ureas, such as N,N'-dihydroxymethyl-4,5-dihydroxyethylene urea;
(j) multifunctional isocyanates, such as toluene diisocyanate, isophorone diisocyanate, methylene diisocyanate, xylene diisocyanate, and hexamethylene diisocyanate;
(k) β-hydroxyalkylamides as disclosed in U.S. Pat. No. 4,076,917, incorporated herein by reference, such as PRIMID™ XL-552, available from EMS-CHEMIE AG, Dornat, Switzerland; and
(l) other crosslinking agents for basic water-absorbing resins known to persons skilled in the art.

A preferred surface crosslinking agent is a dihaloalkane, ethylene glycol diglycidyl ether (EGDGE), PRIMID™ XL-552, or a mixture thereof, which crosslink a basic resin at a temperature of about 25° C. to about 150° C. Especially preferred surface crosslinking agents are dibromoalkanes containing 3 to 10 carbon atoms, EGDGE, and PRIMID™XL-552.

With respect to the acidic water-absorbing resin, suitable surface crosslinking agents are capable of reacting with acid moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of about 25° C. to about 150° C.

Nonlimiting examples of suitable surface crosslinking agents for acidic resins include:

(a) polyhydroxy compounds, such as glycols and glycerol;
(b) metal salts;
(c) quaternary ammonium compounds;
(d) a multifunctional epoxy compound;
(e) an alkylene carbonate, such as ethylene carbonate or propylene carbonate;
(f) a polyaziridine, such as 2,2-bishydroxymethyl butanol tris[3-(1-aziridine propionate]);
(g) a haloepoxy, such as epichlorhydrin;
(h) a polyamine, such as ethylenediamine;
(i) a polyisocyanate, such as 2,4-toluene diisocyanate;
(j) β-hydroxyalkylamides as disclosed in U.S. Pat. No. 4,076,917, incorporated herein by reference, such as PRIMID™ XL-552, available from EMS-CHEMIE AG, Dornat, Switzerland; and
(k) other crosslinking agents for acidic water-absorbing resins known to persons skilled in the art.

In addition to, or in lieu of, surface treating, the SAP material is annealed to improve water absorption and retention properties under a load. It has been found that heating a resin for a sufficient time at a sufficient temperature improves the absorption properties of the resin.

It has been shown that heating an SAP material for about 20 to about 120 minutes at a temperature of about 60° C. to about 200° C. improves absorption properties. Preferably, annealing is performed for about 30 to about 100 minutes at about 80° C. to about 150° C. To achieve the full advantage of annealing, the SAP material is annealed for about 40 to about 90 minutes at about 100° C. to about 140° C. The annealing step can be a separate heating step, or can be performed simultaneously with surface cross-linking of the SAP particle. In preferred embodiments, the SAP material is annealed at a temperature greater than the glass transition temperature, i.e., the Tg, of at least one of the water-absorbing resins present in the SAP material.

To illustrate a present bi-component SAP material, the following examples were prepared and tests performed:

EXAMPLE 7

Powdered poly(vinylamine) (particle size 180–710 μm) was admixed with lightly crosslinked polyacrylic acid (particle size 210–710 μm, 0% neutralized) in a weight ratio of 25% poly(vinylamine) to 75% polyacrylic acid as follows. Poly(vinylamine) and polyacrylic acid gels were prepared by previously described methods at a low crosslinking level. The resulting gels were extruded separately, and dried separately at either 60° C. or 125° C. After complete drying, the polymers were milled and sized to 180–710 μM. The resulting dried granules then were hand mixed and tested. The resulting dry blend was annealed 125° C. to improve performance.

The absorbency characteristics of the resulting bi-component SAP were tested. The results are set forth in Table 4.

TABLE 4

| Mole % EGDGE[1] in PVAm[2] | Mole % MBA[3] in PAA[4] | No Post Treatment | | Post Treatment 1 Hour at 125° C. | |
|---|---|---|---|---|---|
| | | SFC[5] | 4 hr AAP (g/g)[6] | 4 hr AAP SFC | (0.7 psi) (g/g) |
| 4 | 0.35 | 56 | 29.2 | 232 | 41.9 |
| 4 | 0.5 | 265 | 34.2 | 383 | 36.5 |

[1]EGDGE-ethylene glycol diglycidyl ether internal cross-linker;
[2]PVAm-poly(vinylamine);
[3]MBA-methylene bisacrylamide internal crosslinker;
[4]PAA-polyacrylic acid;
[5]SFC-Saline Flow Conductivity; and
[6]AAP-Absorbency against pressure.

Absorbency against pressure (AAP) is the absorptive capacity of superabsorbent polymer (SAP) absorbing against an external pressure of 0.3, 0.7, or 0.9 psi for 1 hour. In this test, a test portion of SAP is weighed and dispersed on the bottom filter screen of a Lexan cylinder. A uniform pressure is applied onto the test portion, and the cylinder apparatus is placed on a filter plate in a petri dish containing saline solution. After a suction time of 1 hour, the cylinder apparatus is removed from the filter plate and weighed to determine the amount of fluid absorbed.

In this test, the SAP is kept in a closed container and allowed to equilibrate to laboratory temperature before removing a test portion for the test. The preferred test conditions are 23±7° C. and 50±10% relative humidity. The sample container should be shaken 3–5 times in order to obtain a homogeneous test portion. Samples should be substantially free of lumps of size greater than 1 mm in diameter before proceeding with testing.

All AAP analyses are performed in duplicate as follows:

a) Assemble one set of apparatus for each sample. The Kel-F cylinder fits snugly into the Lexan cylinder, but can move freely within it.

b) Weight 0.9000±0.005 g of the test portion into a weighing boat, and record the weight of polymer ($W_o$).

c) Carefully scatter the test portion onto the filter screen of the clean and dry cylinder to obtain an even distribution, without shaking. This gives a sample density of about 0.037 g cm$^{-2}$. All samples to be tested are weighed at the same time, but the Kel-F cylinder is not added until immediately prior to starting the test.

d) Place the filter plate in the petri dish or tray.

e) Add the 0.9 saline solution so that the liquid is level with the top of the filter plate.

f) The filter paper is placed on the filter plate, wetting it with the 0.9 saline solution until damp, but not covered by any surface liquid.

g) Place the piston in the cylinder, and weigh, and record the apparatus weight ($A_1$).

h) Add the stainless steel weight to the apparatus, and immediately place the complete assembly on the wet filter paper.

i) Allow to absorb for 1 hour, topping with saline solution as necessary.

j) Lift the assembly above and out of contact with the filter paper and remove the stainless steel weight. This prevents the weight from distorting the mesh in transport to the balance. Weigh and record the weight ($A_2$) of the apparatus.

k) Calculate the absorption against pressure (AAP) for each test portion using the following formula:

$$AAP(g/g) = \frac{A_2 - A_1}{W_o},$$

wherein $W_o$=initial mass of the test portion in g.

$A_1$=mass of dry cylinder apparatus plus sample.

$A_2$=mass of cylinder apparatus plus sample after absorption for 1 hour.

The AAP is the average of the two calculated values, provided that the difference between the values is not greater than 5% of their mean value.

Table 4 shows that a poly(vinylamine)-polyacrylic acid SAP material of the present invention has excellent absorption properties compared to a poly(vinylamine)/polyacrylic acid blend of Table 5 containing a high weight percent of poly(vinylamine), and which is expected to outperform the bi-component SAP materials of Table 4. The bi-component SAP materials of Table 5 were prepared in the same manner as the SAP materials of Table 4, but contained 55 weight % poly(vinylamine) and 45 weight % polyacrylic acid.

TABLE 5

| Drying/Annealing | Mole % EGDGE[1] in PVAm[2] | Mole % MBA[3] in PAA[4] | AUNL | 4 hour AUL (g/g) (0.28 psi) | (0.7 psi) |
|---|---|---|---|---|---|
| Dried at 60° C. | 4 | 0.35 | 57.8 | 45.8 | 37.9 |
| Dried at 60° C. Annealed at 125° C., 1 Hr | 4 | 0.35 | 61.3 | 47.5 | 43.2 |

The present bi-component SAP materials are especially useful in articles designed to absorb and retain liquids, especially electrolyte-containing liquids. Such articles include, for example, diapers and catamenial devices.

To illustrate the improved absorption properties of a bi-component SAP material of the present invention, the blends described in the following Table 6 were prepared and tested for an ability to absorb synthetic urine under a 0.7 psi load. As used here and throughout the specification, poly (AA)-(DN=70) refers to a standard, commercial poly(AA) neutralized about 70% to about 80%, and poly(AA)-(DN=0) refers to unneutralized poly(AA).

TABLE 6

| Sample[1] | Blend Ratio[2] | AUL 0.7 psi (1 hr) | AUL 0.7 psi (3 hr) |
|---|---|---|---|
| 1 | 75/25 | 27.1 | 28.9 |
| 2 | 50/50 | 30.9 | 33 |
| 3 | 25/75 | 35.9 | 40.2 |

[1]Blend of (a) partially neutralized poly(AA) (DN = 70) and (b) a mixture containing 25% by weight poly(vinylamine) and 75% by weight poly(AA) (DN = 0); and
[2]Weight ratio of (a) to (b) in each blend.

The data presented in Table 6 shows the excellent absorption properties achieved by a bi-component SAP material of the present invention in combination with a standard SAP material, like poly(AA) (DN=70).

As illustrated in FIG. 1, a maximum AUL (0.28 psi and 0.7 psi) and AUNL is achieved using superabsorbent material containing about 50 wt % poly(vinylamine) and about 50 wt % poly(acrylic acid), i.e., an AUL (0.7 psi) of 48.9 g of synthetic urine per gram of particles. Surprisingly, a superabsorbent material containing 25 wt % poly(VAm) and 75 wt % poly(AA) demonstrated an AUL (0.7 psi) of about 28 g/g. FIG. 1, and FIGS. 2–8, show that multicomponent superabsorbent particles containing about 20 to about 40 wt % of poly(VAm) exhibit unexpectedly high absorption properties, and are substantially more economical than a bi-component SAP material containing a higher weight percent of poly(VAm).

In particular, FIG. 1 shows that a superabsorbent material exhibits a maximum polyelectrolytic effect when the particles contain about 45 to about 55 wt % polyvinylamine (polyVAm) and about 45 to about 55 wt % poly(AA). However, in FIG. 1, a bi-component superabsorbent material exhibits a second AUL (0.7 psi) maximum between about 20 wt % and about 30 wt %, and particularly between about 25 wt % and about 30 wt % poly(VAm) (about 75 to about 70 wt % poly(AA)). This second AUL (0.7 psi) maxima corresponds to a superabsorbent material optimized for the strongest polyelectrolytic effect attributed to poly (vinylamine).

FIGS. 2–8 show additional plots of AUL or AUNL vs. weight % of poly(vinylamine) in a bi-component SAP material of the present invention further containing poly(AA)(DN=0). In particular, FIGS. 2 and 3 contain plots of AUL (0.7 psi) and AUNL for blends containing 0–100 wt % poly(vinylamine) internally crosslinked with 2 mole % ethylene glycol diglycidyl ether (EGDGE) and 0–100 wt % poly(AA) internally crosslinked with 0.35 mole % methylene bisacrylaminde (MBA).

Figure 2:
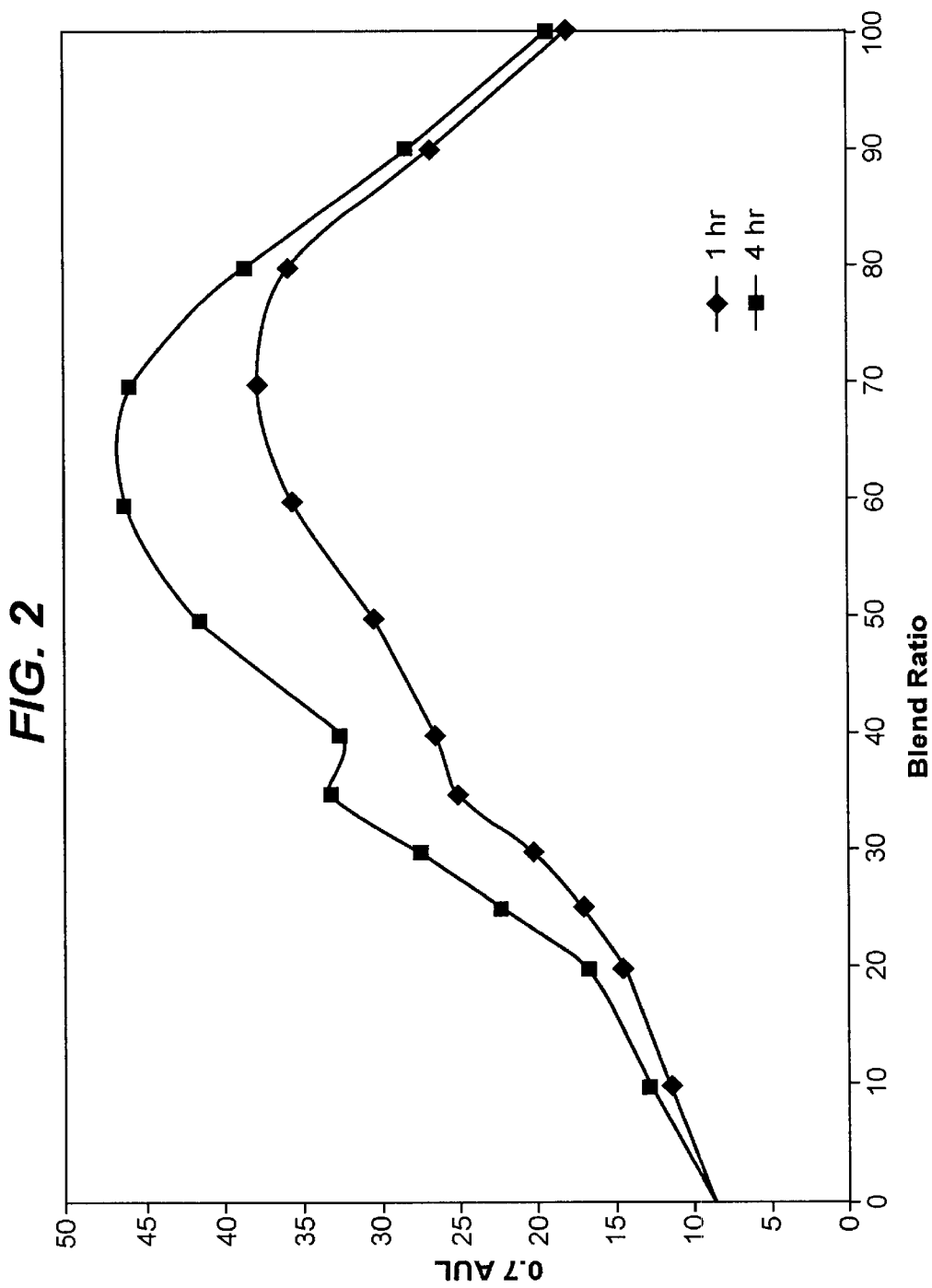
FIGS. 2, 4, 6, and 8 contain plots of wt % poly (vinylamine) in a superabsorbent material vs. AUL (0.7 psi), in g/g, after 1 hour and 4 hours, wherein the poly (vinylamine) and poly(acrylic acid) contain different amounts of internal crosslinker.
Figure 3:
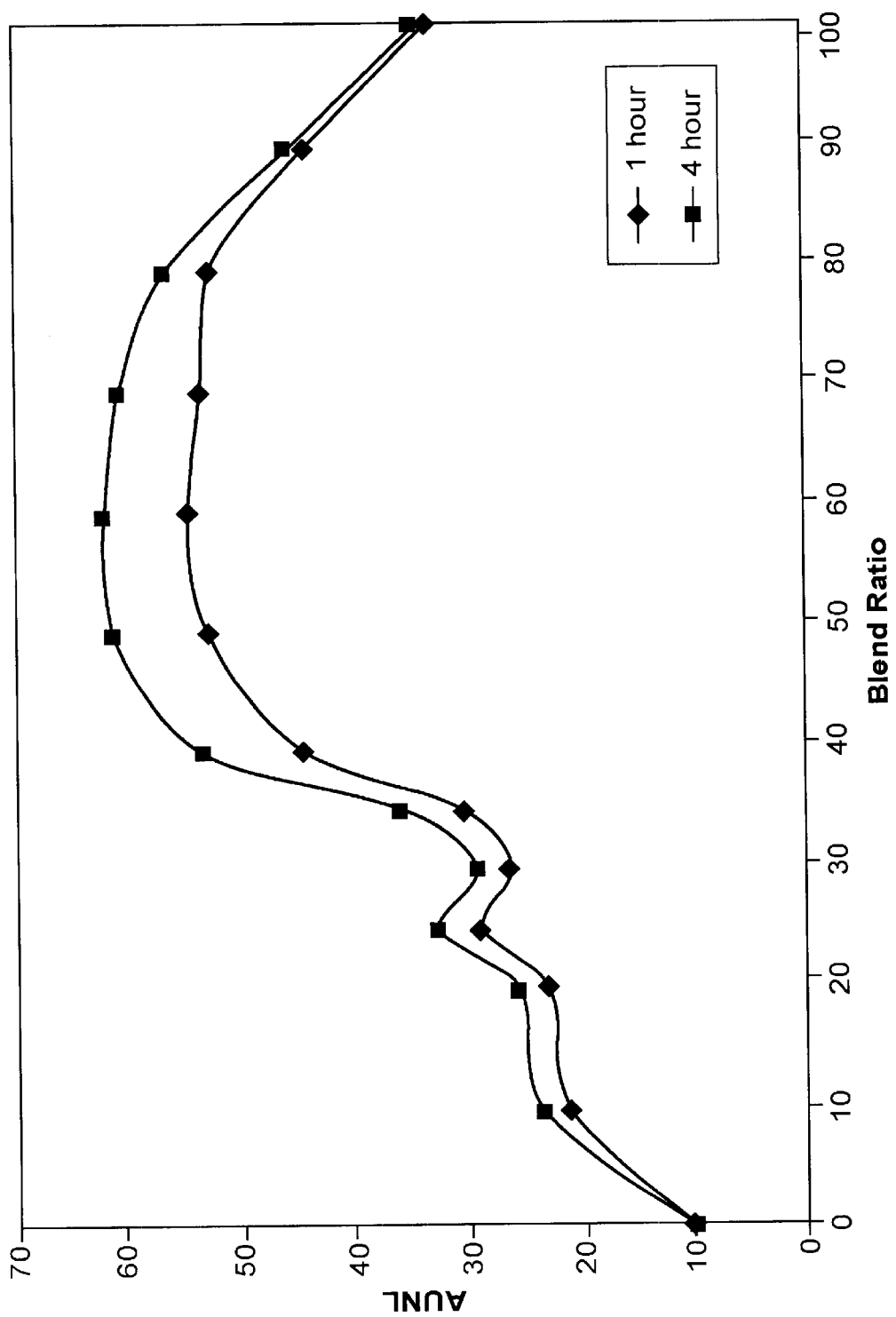
FIGS. 3, 5, and 7 contain plots of wt % poly(vinylamine) in a superabsorbent material vs. AUNL, in 1 g/g, after 1 hour and 4 hours, wherein the poly(vinylamine) and poly(acrylic acid) contain different amounts of internal crosslinker.
Figure 4:
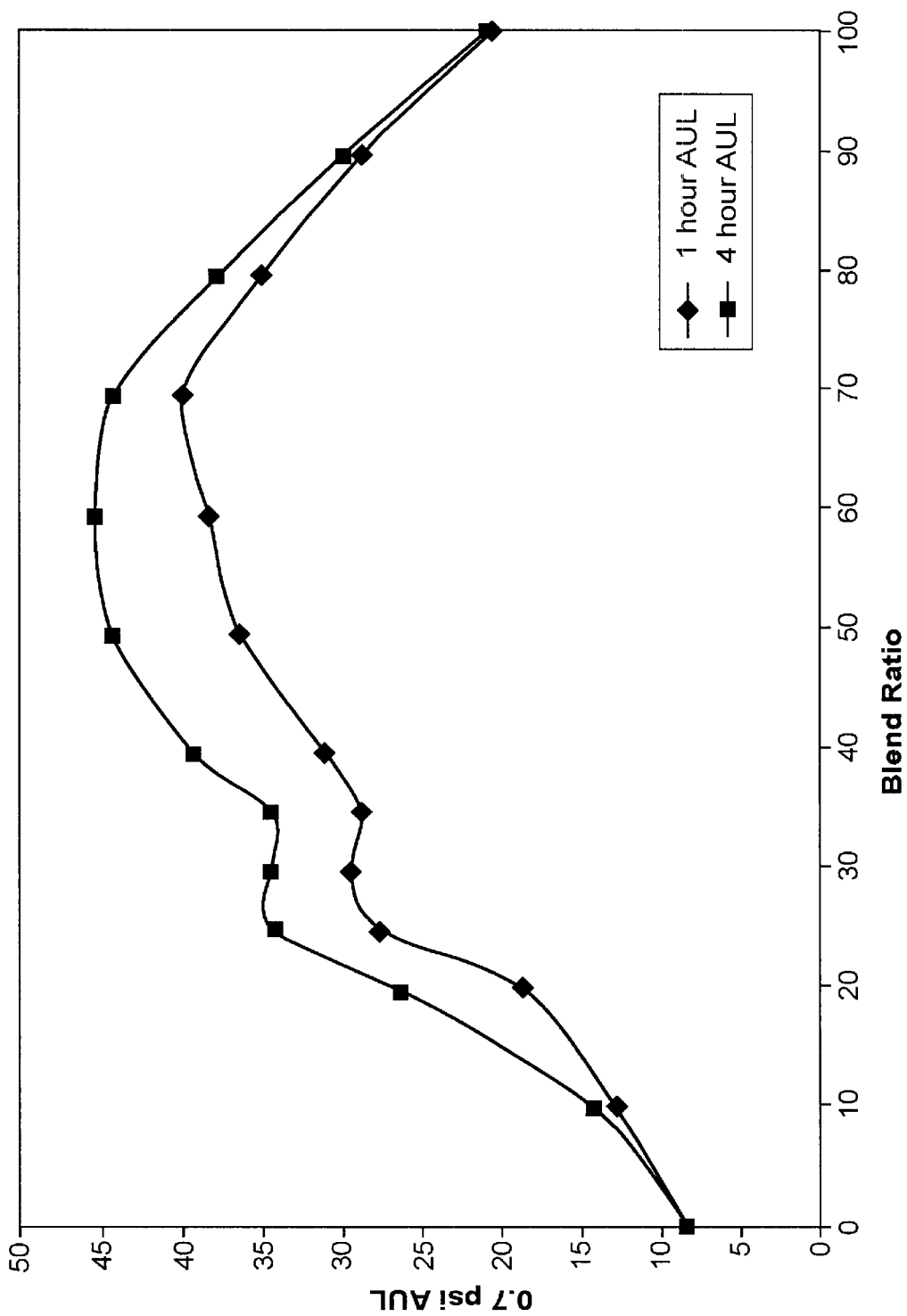
Figure 5:
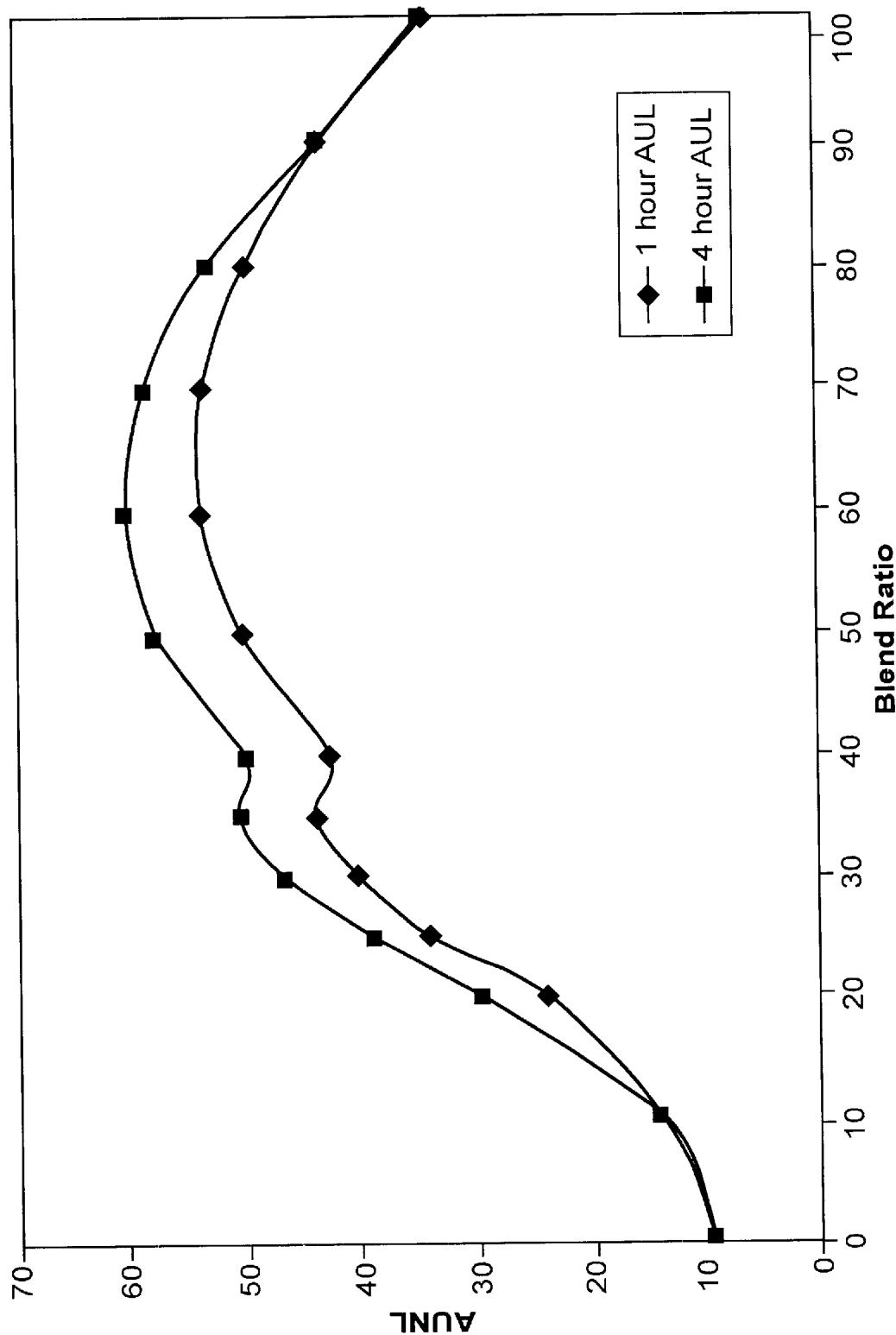

FIGS. 4 and 5 are plots similar to FIGS. 2 and 3, except the poly(vinylamine) is internally crosslinked with 2 mole % EGDGE and the poly(acrylic acid) is internally crosslinked with 0.5 mole % MBA.

Figure 6:
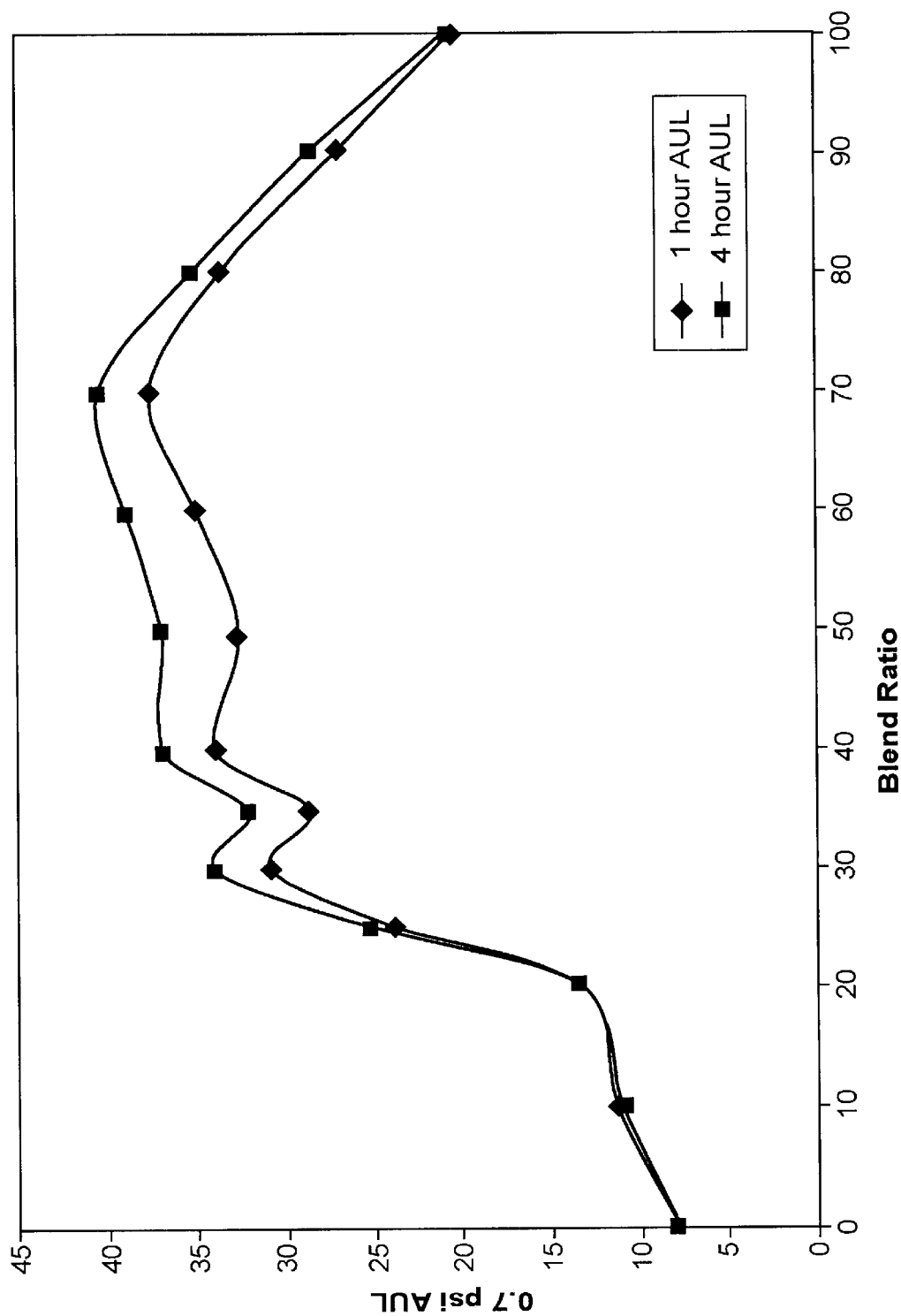
Figure 7:
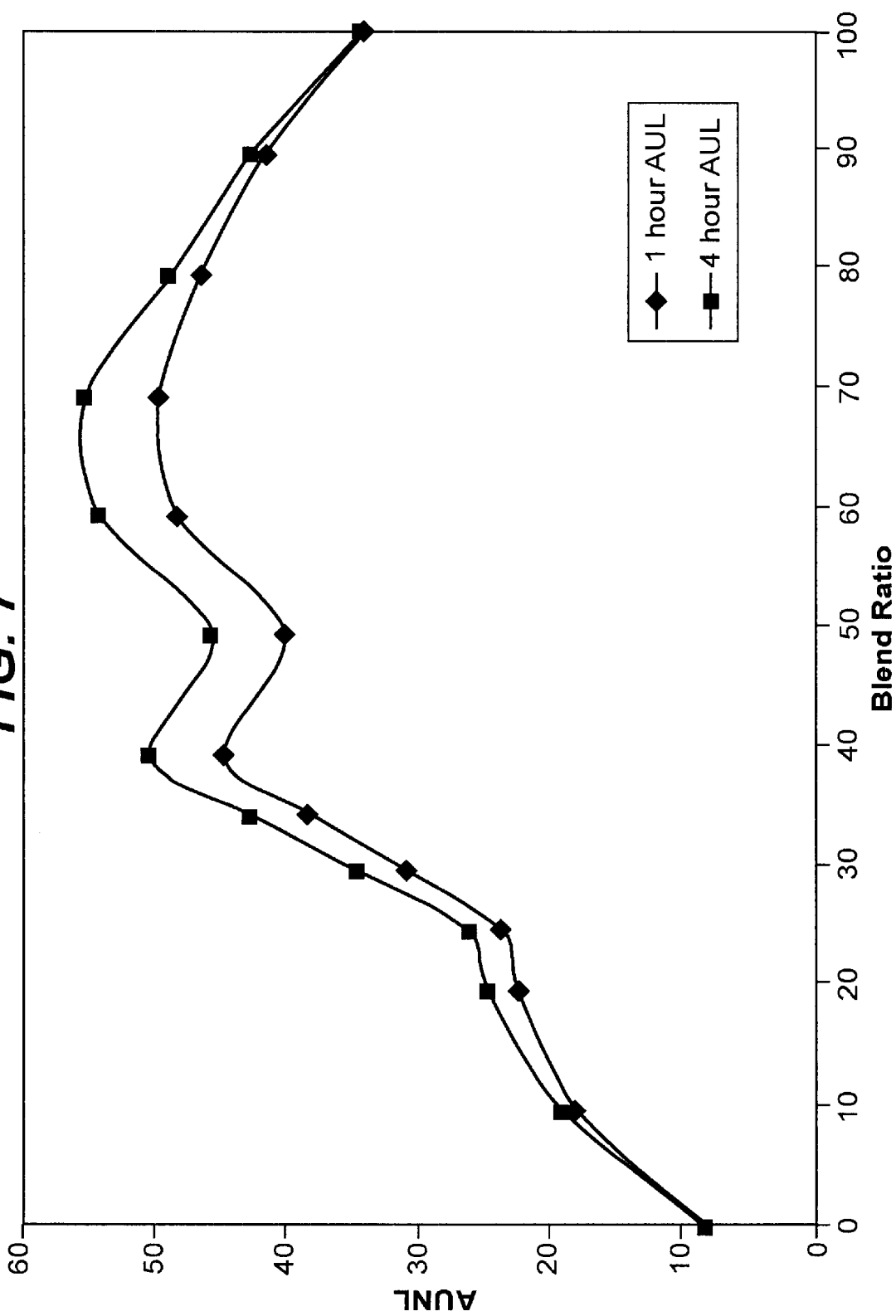

FIGS. 6 and 7 are plots similar to FIGS. 2 and 3, except the poly(vinylamine) is internally crosslinked with 2 mole % EGDGE and the poly(acrylic acid) is internally crosslinked with 1 mole % MBA.

Figure 8:
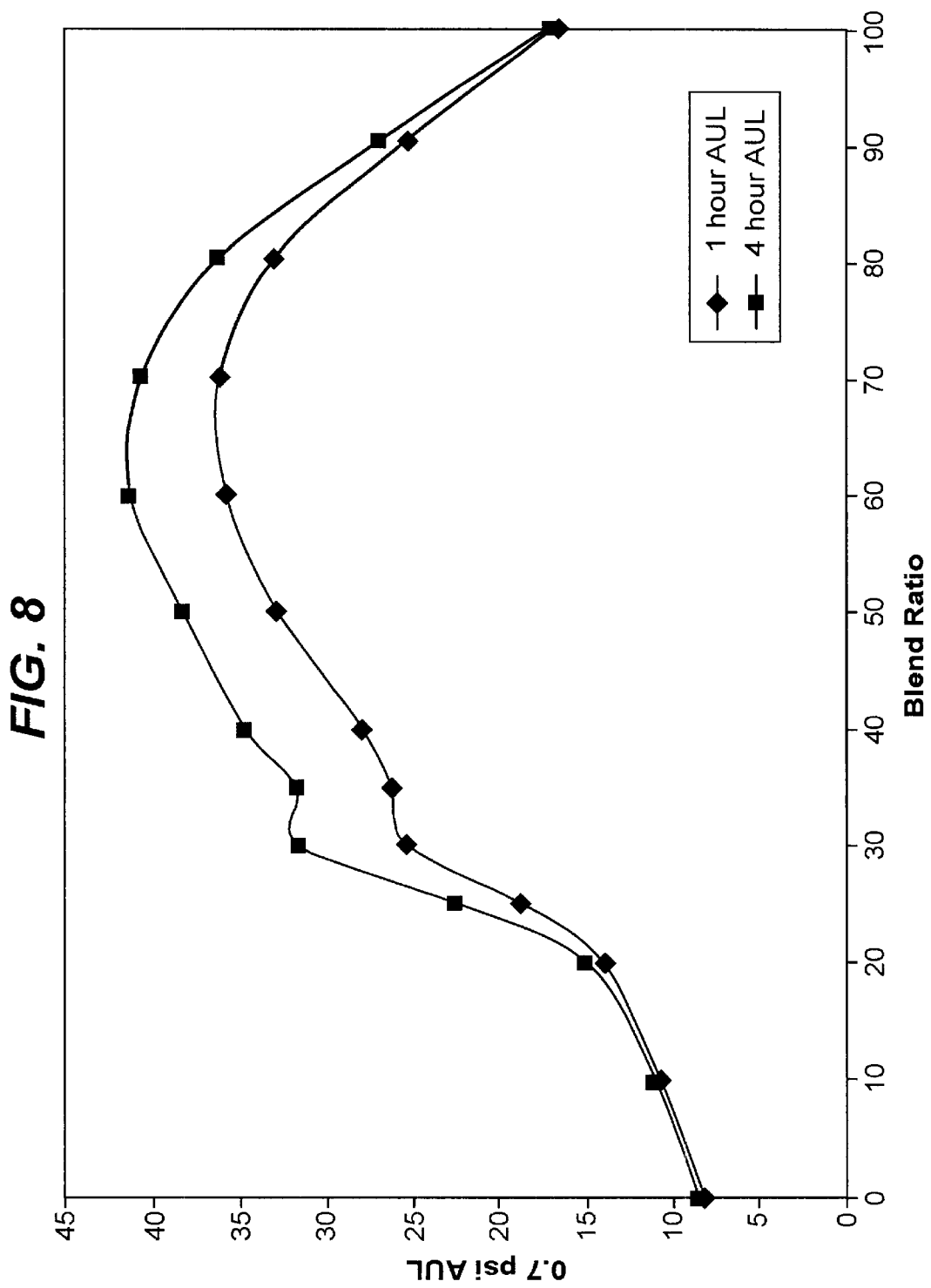

FIG. 8 is a plot similar to FIG. 2, except the poly(vinylamine) is internally crosslinked with 4 mole % EGDGE and the poly(acrylic acid) is internally crosslinked with 0.35 mole % MBA.

FIGS. 1–8 show that the second absorbance maxima, AUL or AUNL, is achieved at about 20 wt % to about 40 wt % of basic resin, based on the total weight of the acidic resin and basic resin. FIGS. 1–8 also show that the second absorbance maxima is partially related to the absolute degree, and to the relative degree, of internal crosslinking of the acidic and basic resins of the bi-component SAP material. However, the second maxima is observed between about 20 wt % and about 40 wt % of basic resin, based on the total weight of the acidic and basic resin, independent of the amount of internal crosslinker present in the acidic or basic resin.

A present SAP material comprising a blend of particles of an acidic resin and particles of a basic resin outperformed a standard poly(AA) absorbent resin. A significant improvement in liquid absorption, both with respect to kinetics and retention, is expected when the standard poly(AA) (DN=70) presently used in diaper cores is replaced by a present SAP material.

The improved results demonstrated by a diaper core containing an SAP material of the present invention also permits the thickness of the core to be reduced. Typically, cores contain 50% or more fluff or pulp to achieve rapid liquid absorption while avoiding problems like gel blocking. Cores which contain a present SAP material acquire liquids sufficiently fast to reduce problems, like gel blocking, and, therefore, the amount of fluff or pulp in the core can be reduced. A reduction in the amount of the low-density fluff results in a thinner core, and, accordingly, a thinner diaper. The SAP in a present core contains an SAP material in an amount of about 15% to 100% of the SAP. The remaining SAP can be a second water-absorbing resin, either basic or acidic.

In summary, an SAP material of the present invention contains a relatively low weight percent of a basic resin, and outperforms conventional SAP particles, e.g., partially neutralized poly(acrylic acid). A present SAP material deionizes an insult solution, e.g., urine, less effectively than an SAP material containing greater than 40 weight % basic resin. However, the polyelectrolyte effect of the basic resin offsets the lesser deionization, while maintaining performance far superior to that of a conventional SAP, as well as exhibiting an improved performance beyond that expected for such a particle.

Poly(vinylamine) works exceptionally well in a present SAP material because its optimum polyelectrolyte effect is predominant only at 50% neutralization. It has been theorized, but not relied upon herein, that this effect is attributed to proton bridges between two amine functionalities to form a ring-like hydrogen bonded structure.

In addition, significant cost savings are achieved by the present SAP material because the amount of expensive basic resin in the bi-component SAP material is reduced. These cost savings are achieved with a minimum reduction in optimum performance, while maintaining a significant performance increase over conventional SAP products.

Many modifications and variations of the invention as hereinbefore set forth can be made without departing from the spirit and scope thereof and, therefore, only such limitations should be imposed as are indicated by the appended claims.

What is claimed is:

1. A superabsorbent material comprising:
   (a) about 20% to about 40%, by weight, of a lightly crosslinked poly(vinylamine), and
   (b) about 60% to about 80%, by weight, of an acidic water-absorbing resin, based on the total weight of the poly(vinylamine) and the acidic resin.

2. The superabsorbent material of claim 1 wherein the poly(vinylamine) is surface crosslinked.

3. The superabsorbent material of claim 2 wherein the poly(vinylamine) is surface crosslinked with up to about 1% of a surface crosslinking agent, by weight of the poly(vinylamine).

4. The superabsorbent material of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylenemaleic anhydride copolymer, an isobutylene-maleic anhydride copolymer, a poly(vinylsulfonic acid), a poly(vinylsulfuric acid), a poly(vinylphosphoric acid), a sulfonated polystyrene, a poly(vinylphosphonic acid), a poly(aspartic acid), and mixtures thereof.

5. The superabsorbent material of claim 1 wherein the poly(vinylamine) and the acidic resin are present in a weight ratio of about 22:78 to about 35:65.

6. The superabsorbent material of claim 1 wherein the poly(vinylamine) and the acidic resin are present in a weight ratio of about 25:75 to about 30:70.

7. An article comprising a superabsorbent material of claim 1.

8. The article of claim 7 wherein the article is a diaper or a catamenial device.

9. A method of absorbing an aqueous medium comprising contacting the medium with a superabsorbent material of claim 1.

10. A method of claim 9 wherein the aqueous medium contains electrolytes.

11. A method of claim 10 wherein the electrolyte-containing aqueous medium is selected from the group consisting of urine, saline, menses, and blood.

12. A superabsorbent material comprising about 20% to about 40%, by weight, of one or more basic water-absorbing resin and about 60% to about 80%, by weight, of one or more acidic resin, based on the total weight of the basic and acidic resin.

13. The particle of claim 12 having a weight ratio of acidic resin to basic resin of about 78:22 to about 65:35.

14. The particle of claim 12 having a weight ratio of acidic resin to basic resin of about 75:25 to about 70:30.

15. The particle of claim 12 having a mole ratio of basic resin to acidic resin of about 0.4:1 to about 0.9:1.

16. The particle of claim 12 having a weight ratio of acidic resin to basic resin of about 0.45:1 to about 0.85:1.

17. The particle of claim 12 having a weight ratio of acidic resin to basic resin of about 0.55:1 to about 0.75:1.

18. The particle of claim 12 wherein the material is annealed at a temperature of about 60° C. to about 200° C. for about 20 to about 120 minutes.

19. The particle of claim 12 wherein the basic resin is lightly crosslinked and has about 75% to 100% basic moieties present in a free base form.

20. The particle of claim 12 wherein at least 6% of the monomer units comprising the basic resin are basic monomer units.

21. The particle of claim 12 wherein the basic resin is selected from the group consisting of a poly(vinylamine), a polyethylenimine, a poly(allylguanidine), a poly(allylamine), a poly(diallylamine), a polyazetidine, and mixtures thereof.

22. The particle of claim 12 wherein the acidic resin contains a plurality of carboxylic acid, sulfonic acid, sulfuric acid, phosphonic acid, or phosphoric acid groups, or a mixture thereof.

23. The particle of claim 12 wherein the acidic resin is lightly crosslinked and has about 75% to 100% acid moieties present in the free acid form.

24. The particle of claim 12 wherein at least 10% of the monomer units comprising the acidic resin are acidic monomer units.

25. The particle of claim 12 wherein the basic resin comprises a poly(vinylamine), a poly(vinylguanidine), a polyethylenimine, or a mixture thereof, and the acidic resin comprises poly(acrylic acid).

26. An article comprising a multicomponent superabsorbent particle of claim 12.

27. An article comprising a core containing a superabsorbent material of claim 12, said core comprising about 10% to 100% by weight of the superabsorbent material.

28. A diaper having a core, said core comprising at least 25% by weight of a superabsorbent material of claim 12.

29. The diaper of claim 28 wherein the core comprises at least 50% by weight of the superabsorbent material.

30. The diaper of claim 28 wherein the core comprises at least 75% by weight of the superabsorbent material.

31. The diaper of claim 28 wherein the core further comprises an acidic water-absorbing resin neutralized from 25 to 100%.

32. The diaper of claim 28 further comprising a topsheet in contact with a first surface of the core, and a backsheet in contact with a second surface of the core, said second core surface opposite from said first core surface.

33. The diaper of claim 32 further comprising an acquisition layer disposed between the topsheet and the core.

* * * * *

UNITED STATES PATENT AND TRADEMARK OFFICE
CERTIFICATE OF CORRECTION

PATENT NO. : 6,603,055 B2  Page 1 of 1
DATED : August 5, 2003
INVENTOR(S) : Michael A. Mitchell et al.

It is certified that error appears in the above-identified patent and that said Letters Patent is hereby corrected as shown below:

<u>Title page,</u>
Item [54], Title, "poly(Vinylamine) –Base" should be -- Poly(vinylamine) –Based --

Signed and Sealed this

Twentieth Day of April, 2004

JON W. DUDAS
*Acting Director of the United States Patent and Trademark Office*